US006458753B1

(12) United States Patent
Haylett

(10) Patent No.: US 6,458,753 B1
(45) Date of Patent: *Oct. 1, 2002

(54) ABRASIVE CLEANING COMPOSITIONS

(75) Inventor: Nicholas Haylett, Marlow Bottom (GB)

(73) Assignee: Reckitt Benckiser (UK) Limited, Slough (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 140 days.

(21) Appl. No.: 09/331,281

(22) PCT Filed: Dec. 22, 1997

(86) PCT No.: PCT/GB97/03521

§ 371 (c)(1),
(2), (4) Date: Aug. 11, 1999

(87) PCT Pub. No.: WO98/29525

PCT Pub. Date: Jul. 9, 1998

(30) Foreign Application Priority Data

Dec. 31, 1996 (GB) .............................................. 9627099
Feb. 7, 1997 (GB) .............................................. 9702569

(51) Int. Cl.$^7$ .............................. C11D 1/62; C11D 3/14
(52) U.S. Cl. ....................... 510/384; 510/386; 510/387; 510/391; 510/397; 510/399; 510/421; 510/435; 510/471; 510/473; 510/478; 510/504; 510/509; 510/395

(58) Field of Search ................................. 510/384, 386, 510/387, 391, 397, 399, 421, 435, 471, 473, 478, 504, 509

(56) References Cited

U.S. PATENT DOCUMENTS

| 3,577,347 A | | 5/1971 | Monick ........................ 252/99 |
| 3,997,460 A | * | 12/1976 | Sirine et al. .................. 252/106 |
| 4,561,993 A | | 12/1985 | Choy et al. ............. 252/174.25 |
| 5,435,935 A | | 7/1995 | Kupneski ..................... 252/156 |
| 5,690,539 A | * | 11/1997 | Swidler et al. ................ 451/38 |
| 5,756,442 A | * | 5/1998 | Jeschke et al. .............. 510/236 |

FOREIGN PATENT DOCUMENTS

| EP | WO 91/08282 | * | 6/1991 | ........... C11D/17/00 |
| WO | WO91/08282 | | 6/1991 | ........... C11D/17/00 |

OTHER PUBLICATIONS

WPI Database Section Ch, Week 8302, Derwent Publications Ltd., AN 83–03645K XP002067677 & JP 57–95199 A, Nov. 30, 1982.
Copy of PCT International Search Report for PCT/GB97/03521 dated Jun. 22, 1998.

* cited by examiner

Primary Examiner—Yogendra N. Gupta
Assistant Examiner—Brian P. Mruk
(74) Attorney, Agent, or Firm—Fish & Richardson P.C.

(57) ABSTRACT

An abrasive cleaning composition comprises abrasive particles, preferable of a soluble abrasive, cationic or non ionic surfactants and a quaternary ammonium antibacterial agent.

15 Claims, No Drawings

ABRASIVE CLEANING COMPOSITIONS

BACKGROUND OF THE INVENTION

The present invention relates to cleaning compositions, and in particular to cleaning compositions containing abrasive particles.

Cleaning compositions containing abrasive particles are well known and may generally be classified into two types. The first type contain water-insoluble abrasive particles. These particles are often difficult to rinse away from the cleaned surface and can leave an undesirable gritty residue on the surface. In order to overcome these disadvantages, the second type of composition has been proposed in which the abrasive particles are water soluble. These compositions contain the water-soluble abrasive particles in an amount greater than that required to achieve a saturated solution. Thus, undissolved abrasive particles are always present in the composition. Because the abrasive particles are water soluble, particles remaining on the surface after cleaning tend to be dissolved on rinsing the surface and are thus removed from the surface. Cleaning compositions containing water soluble abrasive particles are described in EP 0 193 375 and WO 91/08282.

Cleaning compositions of this general type are particularly suitable for cleaning hard surfaces especially in kitchens and bathrooms such as sinks, washbasins, baths, shower trays and stalls, lavatories, work surfaces and the like. In these uses, the concept of good hygiene is particularly important to consumers and to meet this need, abrasive cleaning compositions having soluble or insoluble abrasive particles and further including a chlorine containing, in particular a hypochlorite containing bleach, have been proposed. The hypochlorite bleach is included in the compositions to provide, inter alia, an antibacterial effect. U.S. Pat. No. 3,577,347 describes a composition consisting of anionic and non-ionic detergents, a chlorine bleaching compound and more than 50% by weight of a water soluble abrasive salt having less than six molecules of water of hydration and selected from alkali and alkaline earth metal salts. As is well known, the inclusion of chlorine containing bleaches in cleaning compositions causes significant formulation problems with regard, in particular, to the stability of the composition and the thickening of the composition. Furthermore, chlorine containing bleaches are often perceived by the consumer as "aggressive" or "harsh" and may easily damage clothes, soft furnishings and the like.

Accordingly, the present invention seeks to overcome the above disadvantages and to provide a cleaning composition containing an abrasive, especially a water-soluble abrasive which composition also has antibacterial properties, without requiring the incorporation of bleaching agents.

Two further relevant prior art documents are as follows.

U.S. Pat. No. 3,997,460 describes a surface adherent abrasive liquid cleaner including a mineral acid to aid in dissolving stains and an abrasive suspended in the cleaner to aid in mechanically scrubbing off stains.

U.S. Pat. No. 4,561,993 describes a thixotropic cleaner comprising about 6 to 12% of precipitated silica, about 0.05 to 2.5 of a cationic, nonionic, zwitteronic or amphoteric surfactant or mixtures thereof that has the ability to hydrogen bond, an acid and an abrasive.

One known method of providing antibacterial properties in a cleaning composition is to include in the composition a quaternary ammonium type antibacterial agent. Such quaternary ammonium compounds are included in known (non-abrasive) antibacterial hard surface cleaners. However, the inclusion of quaternary ammonium antibacterial agents presents disadvantages in formulating cleaning compositions. For example, due to the cationic nature of the quaternary ammonium compounds, conventional anionic surfactants or surfactant mixtures containing anionic surfactants cannot be used. Also, the inclusion of quaternary ammonium compounds often presents formulations difficulties with thickening media such as polyacrylates and synthetic or natural clays such as Laponite (TM) and some Bentonite types. Furthermore, it has commonly been supposed that the cationic quaternary ammonium compounds would become absorbed on anionic sites of the abrasive particles, thereby significantly reducing or rendering ineffective the antibacterial properties of these compounds.

SUMMARY OF THE INVENTION

However it has now been shown that useful antibacterial properties can be obtained from hard surface cleaning compositions containing both quaternary ammonium compounds and abrasive particles, in particular particles of a soluble abrasive material. Accordingly, the present invention provides an aqueous antibacterial abrasive cleaning composition comprising, in addition to water, 8% to 80% of abrasive particles, 0.5% to 25% of a cationic or non-ionic surfactant, 0.1% to 10% of a quaternary ammonium antibacterial agent, 0% to 15% of a solvent, and a functional amount of a thickening agent, wherein the abrasive particles are soluble in the composition and are present in an amount in excess of their saturation solubility.

Preferably the abrasive particles are water-soluble abrasive particles is selected from inorganic or organic water soluble salts of alkali or alkaline earth metals. They are present in the composition in an amount such that at least 5% of the particles (by weight of the composition) remain undissolved.

DETAILED DISCLOSURE

Preferred abrasive particles include sodium carbonate, sodium bicarbonate, sodium sesquicarbonate sodium tripolyphosphate pentahydrate, sodium tetraborate decahydrate, potassium sulphate and sodium citrate. Additionally or alternatively, other water soluble salts may be included, such as sodium chloride, potassium chloride, magnesium chloride, calcium chloride and other inorganic or organic water soluble salts of lithium, magnesium, sodium, potassium and calcium, of which sodium oxalate, sodium succinate, sodium adipate and sodium glutarate are examples.

As indicated above, the soluble abrasive particles must be present in an amount in excess of the saturation solubility, so that in the composition the soluble salt comprising the abrasive particles is present in both the dissolved and the undissolved state. Preferably, the salt is present in total in an amount of 15% to 60%, particularly 30% to 50%, and especially about 40% by weight of the composition.

One of the criteria used in selecting the abrasive particles is the hardness of the particles. The particles should have a hardness less than that of the surfaces to be cleaned, in order to avoid scratching the surfaces. Thus, the particles will usually have a hardness less than that of plastic, for example acrylic, baths and like materials. A Mohs hardness of at least 2 and less than 4, preferably less than 3 will in general be suitable.

In order to provide the necessary abrasive properties, the abrasive particles will usually have a mean particle diameter of from 5 mm to 500 mm, and preferably from 10 mm to 300 mm. The mean particle diameter may also have an effect on the ability of compositions to maintain the abrasive particles in suspension, and also on the cleaning efficacy.

It is important that the compositions of the invention are stable in use and storage so that the abrasive particles remain in suspension. It may usually be expected that the compositions will be stored and used at temperatures generally within the range of 0° C. to 40° C. It is therefore preferable to choose salts for the abrasive particles whose saturation solubility changes to the minimum extent over this temperature range. Particularly, it is preferable that the saturation solubility of the salt in water at 40° C. is less than 10 times, most preferably less than 8 times, and especially less than 2 times that at 10° C. Suitable salts will typically have a solubility in the range of from about 2 g to about 70 g per 100ml of water and 0° C. and from about 4 g to about 150 g per 100ml of water at 40° C. More preferably the salts will have a solubility in the range of from about 3 g to about 70 g per 100 ml of water at 0° C. and from about 4 g to about 90 g per 100 ml of water at 40° C. and especially from about 8 g to about 35 g per 100 ml at 0° C. and from about 12 g to about 40 g per 100 ml of water at 40° C.

To ensure that the composition contains undissolved abrasive particles, the salt forming the abrasive particles will preferably have a saturation solubility at 10° C. of not more than 15% by weight. In order to ensure that the abrasive particles may easily be rinsed from the surface after cleaning, the salt will preferably have a solubility in water of at least 5 g/l at 10° C.

The compositions of the invention will preferably have a pH in the range from pH 5 to pH 12, more preferably from pH 7 to pH 12 and especially from pH 8 to pH 12.

Of the above mentioned salts, sodium bicarbonate meets the above-noted criteria particularly well and is preferred in the present invention.

The quaternary ammonium antibacterial agents used in the present invention may in general be selected from those known in the art. Suitable examples include quaternary ammonium compounds and salts thereof which may be characterised by the general structural formula:

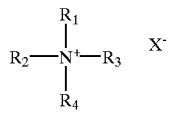

where at least one $R_1$, $R_2$, $R_3$ and $R_4$ is a hydrophobic, aliphatic, aryl aliphatic or aliphatic aryl radical of from 6 to 26 carbon atoms, and the entire cation portion of the molecule has a molecular weight of at least 165. The hydrophobic radicals may be long-chain alkyl, long-chain alkoxy aryl, long-chain alkyl aryl, halogen-substitued long-chain alkyl aryl, long-chain alkyl phenoxy alkyl, aryl alkyl, etc. The remaining radicals on the nitrogen atoms other than the hydrophobic radicals are substituents of a hydrocarbon structure usually containing a total of no more than 12 carbon atoms. The radicals $R_1$, $R_2$, $R_3$ and $R_4$ may be straight chained or may be branched, but are preferably straight chained, and may include one or more amide or ester linkages. The radical X may be any salt-forming anionic radical.

Exemplary quaternary ammonium salts within the above description include the alkyl ammonium halides such as decyl trimethyl ammonium chloride, decyl dimethyl benzyl ammonium chloride, lauryl trimethyl ammonium chloride, lauryl dimethyl benzyl ammonium chloride, myristyl trimethyl ammonium chloride, myristyl dimethyl benzyl ammonium chloride, myristyl trimethyl ammonium bromide, cetyl trimethyl ammonium chloride, cetyl trimethyl ammonium bromide, dioctyl dimethyl ammonium chloride, didecyl dimethyl ammonium chloride and dilauryl dimethyl ammonium chloride, alkyl aryl ammonium halides such as octadecyl dimethyl benzyl ammonium bromide, N-alkyl pyridinium halides such as N-cetyl pyridinium bromide, and the like. Other suitable types of quarternary ammonium salts include those in which the molecule contains either amide or ester linkages such as octyl phenoxy ethoxy ethyl dimethyl benzyl ammonium chloride, N-(laurylcocoaminoformlmethyl)-pyridinium chloride, and the like. Other very effective types of quarternary ammonium compounds which are useful as antibacterial agents include those in which the hydrophobic radical is characterised by a substituted aromatic nucleus as in the case of lauryloxyphenyltrimethyl ammonium chloride, cetyl aminophenyltrimethyl ammonium methosulfate, dodecyl phenyltrimethyl ammonium methosulfate, dodecylbenzyl trimethyl ammonium chloride, chlorinated dodecylbenzyltrimethyl ammonium chloride, and the like.

Preferred quaternary ammonium compounds which act as antibacterial agents and which are be found useful in the practice of the present invention include those which have the structural formula:

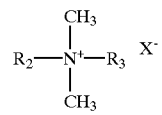

wherein $R_2$ and $R_3$ are the same or different $C_8$–$C_{12}$ alkyl groups, or $R_2$ is $C_{12-16}$ alkyl, $C_{8-18}$ alkylethoxy, $C_{8-18}$ alkylphenolethoxy group and $R_3$ is a benzyl group and X may be any salt-forming anionic radical, but is preferably a halide, such as a chloride, bromide or iodide, or is a methosulfate radical. The alkyl groups recited in $R_2$ and $R_3$ may be straight chained or branched, but are preferably substantially linear.

Such quatenary ammonium antibacterial agents are usually sold as mixtures of two or more different quatenaries, such as BARDAC 205M (presently commercially available from Lonza, UK Ltd) which is believed to be a 50% aqueous solution containing 20% by weight of an alkyl dimethyl benzylammonium chloride (50% C14, 40% C16 alkyl); 15% by weight of an octyl decyl dimethylammonium chloride; 7.5% by weight of dioctyl dimethylammonium chloride; and 7.5% by weight of didecyl dimethylammonium chloride. A further useful quarternary ammonium antibacterial agent is CYNCAL® 80% (presently commercially available from Hilton Davis Chemical Co.;) which is believed to comprise 80% by weight of an alkyl dimethyl benzylammonium chloride (50% C14, 40% C12 and 10% C16 alkyl), 10% water and 10% ethanol. Further useful quaternary ammonium antibacterial agents include BTC-8358®, an alkyl benzyl dimethyl ammonium chloride (80% active) and BTC-818®, a dialkyl dimethyl ammonium chloride (both presently commercially available from the Millchem UK Ltd). Additional suitable commercially available quaternary ammonium antibacterial agents of the alkyl dimethyl benzyl ammonium chloride type containing the same dimethyl benzyl ammonium chloride mixture as that of CYNCAL® and which are generally referred to as quarternium salts include BARQUAT® MB-80, (presently commercially available from Lonza, UK Ltd.) which is believed to be an 80% by weight solution (20% ethanol) of the quarternary, HYAMINE 1622 believed to be an aqueous solution of benzethonium chloride and HYAMINE 3500, which is believed to be a 50% aqueous solution of the quarternary (both presently commercially available from Lonza UK, Ltd).

Preferably, the quaternary ammonium antibacterial agent is present in an amount of from 0.1% to 4%.

Suitable nonionic surfactants which can be used in the instant invention include water soluble nonionic surfactants, many of which are well known and conventionally used in the art. Nonlimiting examples of nonionic surfactants which may be employed in the composition include those which are water soluble or water miscible and include one or more of the following: amine oxides, block copolymers, alkoxylated alkanolamides, ethoxylated alcohols, and ethoxylated alkyl phenols, and the like. Other commercially available nonionic surfactants may be found in the "Chemical Classification" section of McCutcheon's *Emulsifier & Detergents North American Edition,* 1991 and also in *Surfactants Europa,* 3rd edn. Hollis (Ed) 1995.

Useful water soluble nonionic surfactants in the compositions according to the present invention include commercially well known surfactant compositions, including the primary aliphatic alcohol ethoxylates, secondary aliphatic alcohol ethoxylates, alkylphenol ethoxylates and ethylene-oxide-propylene oxide condensates of primary alkanols. These water soluble nonionic surfactants are generally the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with a hydrophilic group containing an ethylene oxide and/or the polyhydration product thereof, polyethylene glycol, to form a water soluble nonionic surfactant.

Useful nonionic surfactants include the condensation products of a higher alcohol (e.g. an alkanol containing about 8 to 18 carbon atoms in a straight or branched chain configuration) condensed with about 5 to 30 moles of ethylene oxide, for example, lauryl or myristyl alcohol condensed with about 16 moles of ethylene oxide, tridecanol condensed with about 6 to 10 moles of ethylene oxide, myristyl alcohol condensed with about 10 moles of ethylene oxide per mole of myristyl alcohol, the condensation product of ethylene oxide with a cut of coconut fatty alcohol containing a mixture of fatty alcohols with alkyl chains varying from 10 to about 14 carbon atoms in length and wherein the condensate contains either about 6 moles of ethylene oxide per mole of total alcohol or about 9 moles of ethylene oxide per mole of alcohol and tallow alcohol ethoxylates containing 6 moles ethylene oxide to 11 moles ethylene oxide per mole of alcohol.

A preferred group of the foregoing nonionic surfactants are certain ethoxylates presently commercially available under the trade name Neodol® (Shell Chemical) which are believed to be higher aliphatic, primary alcohols containing about 9–15 carbon atoms, such as $C_9$–$C_{11}$ alkanol condensed with 8 moles of ethylene oxide (Neodol 91-8), $C_{12-13}$ alkanol condensed with 6.5 moles ethylene oxide (Neodol® 23-6.5), $C_{12-15}$ alkanol condensed with 12 moles ethylene oxide (Neodol® 25-12), $C_{14-15}$ alkanol condensed with 13 moles ethylene oxide (Neodol® 45-13), and the like. Such ethoxylates have an HLB (hydrophobic to lipophilic balance) value of about 8 to 15 and give good oil/water emulsification, whereas ethoxylates with HLB values below 8 contain less than 5 ethylene oxide groups and tend to be poor emulsifiers and poor detergents.

Additional satisfactory nonionic surfactant compositions include the condensation products of a secondary aliphatic alcohols containing 8 to 18 carbon atoms in a straight or branched chain configuration condensed with 5 to 30 moles of ethylene oxide. Examples of commercially available nonionic detergents of the foregoing type are those presently commercially available under the trade name of Tergitol® (Union Carbide Ltd) such as Tergitol 15-S-12 which is described as being $C_{11}$-$C_{15}$ secondary alkanol condensed with 9 ethylene oxide units, or Tergitol 15-S-9 which is described as being $C_{11}$–$C_{15}$ secondary alkanol condensed with 12 ethylene oxide units per molecule.

Other suitable nonionic surfactant compositions include the polyethylene oxide condensates of one mole of alkyl phenol containing from about 8 to 18 carbon atoms in a straight-or branched chain alkyl group with about 5 to 30 moles of ethylene oxide. Specific examples of alkyl phenol ethoxylates include nonyl phenol condensed with about 9.5 moles of ethylene oxide per mole of nonyl phenol, dinonyl phenol condensed with about 12 moles of ethylene oxide per mole of phenol, dinonyl phenol condensed with about 15 moles of ethylene oxide per mole pf phenol and diisoctylphenol condensed with about 15 moles of ethylene oxide per mole of phenol. Commercially available nonionic surfactants of this type include those which are presently commercially available under the trade name of Igepal® (Rhone-Poulenc, Chemicals Ltd).

Also among the satisfactory nonionic surfactants which find use with the present inventive compositions are the water-soluble condensation products of a $C_8$–$C_{20}$ alkanol with a mixture of ethylene oxide and propylene oxide wherein the weight ratio of ethylene oxide to propylene oxide is from 2.5:1 to 4.1, preferably 2.89:1 to 3.3:1, with the total of the ethylene oxide and propylene oxide (including the terminal ethanol or proponol group) being from 60–85%, preferably 70 to 80%, by weight. Such surfactants include those which are presently commercially available under the trade name of Plurafac® (BASF plc). Further useful water-soluble condensation products of a $C_8$–$C_{20}$ alkanol with a mixture of ethylene oxide and/or propylene oxide include those which are presently marketed under the trade name Poly-Tergent SL (Olin UK Ltd) series of nonionic surfactants which are cited to comprise between 5 and 12 moles of oxyethylene per molecule.

Other suitable water-soluble nonionic detergents which are less preferred but which are nonetheless useful are those which are marketed under the trade name Pluronics® (BASF plc). The compounds are formed by condensing ethylene oxide with a hydrophobic base formed by the condensation of propylene oxide with propylene glycol The molecular weight of the hydrophobic portion of the molecule is of the order of 950 to 4,000 and preferably 200 to 2,500. The addition of polyoxyethylene radicals of the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants are in liquid form and particularly satisfactory surfactants are available as those marketed as Pluronics® L62 and Pluronics L64.

Alkylmonoglyocosides and alkylpolyglycosides which find use in the present inventive compositions include known nonionic surfactants which are alkaline and electrolyte stable. Alkylmonoglycosides and alkylpolyglycosides are prepared generally by reacting a monosaccharide, or a compound hydrolyzable to a monosaccharide with an alcohol such as a fatty alcohol in an acid medium. Various glycoside and polyglycoside compounds including alkoxylated glycosides and processes for making them are disclosed in U.S. Pat. Nos. 2,974,134; 3,219,656; 3,598,865; 3,640,998; 3,707,535, 3,772,269; 3,839,318; 3,974,138; 4,223,129 and 4,528,106.

One exemplary group of such useful alkylpolyglycosides include those according to the formula:

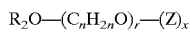

where Z is derived from glucose, $R_2$ is a hydrophobic group selected from alkyl groups, alkylphenyl groups, hydroxyalkylphenyl groups as well as mixtures thereof, wherein the alkyl groups may be straight chained or branched, which contain from about 8 to about 18 carbon atoms, n is 2 or 3, r is an integer from 0 to 10, but is preferably 0, and x is a value from about 1 to 8, preferably from about 1.5 to 5. Preferably the alkylpolyglycosides are nonionic fatty alkylpolyglucosides which contain a straight chain or branched chain $C_8$–$C_{15}$ alkyl group, and have an average of from about 1 to S glucose units per fatty alkylpolyglucoside molecule. More preferably, the nonionic fatty alkylpolyglucosides which contain straight chain or branched $C_8$–$C_{15}$ alkyl group, and have an average of from about 1 to about 2 glucose units per fatty alkylpolyglucoside molecule.

A further exemplary group of alkyl glycoside surfactants suitable for use in the practice of this invention may be presented by formula I below:

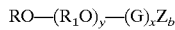     I wherein: R is a monovalent organic radical containing from about 6 to about 30, preferably from about 8 to 18 carbon atoms; $R_1$ is a divalent hydrocarbon radical containing from about 2 to about 4 carbon atoms; y is a number which has an average value from about 0 to about 1 and is preferably 0, G is a moiety derived from a reducing saccharide containing 5 or 6 carbon atoms; and x is a number having an average value from about 1 to 5 (preferably from 1.1 to 2); Z is $O_2M^1$,

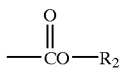

$O(CH_2)$, $CO_2M^1$, $OSO_3M^1$, or $O(CH_2)SO_3M^1$; $R_2$ is $(CH_2)CO_2M^1$ or $CH=CHCO_2M^1$; (with the proviso that Z can be $O_2M^1$ only if Z is in place of a primary hydroxyl group in which the primary hydroxyl-bearing carbon atom, —CH2OH, is oxidized to form a

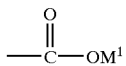

group) b is a number of from 0 to 3x+1 preferably an average of from 0.5 to 2 per glycosal group; p is 1 to 10, $M^1$ is $H^+$ or an organic or inorganic counterion, particularly cations such as, for example, an alkali metal cation, ammonium cation, monoethanolamine cation or calcium cation.

As defined in Formula 1 above, R is generally the residue of a fatty alcohol having from about 8 to 30 and preferably 8 to 18 carbon atoms. Examples of such alkylglycosides as described above include, for example APG™325 CS Glycoside® which is described as being a 50% $C_9$–$C_{11}$ alkyl polyglycoside, also commonly referred to as D-glucopyranoside, (commercially available from Henkel Ltd) and Glucopon™ 625 CS which is described as being a 50% $C_{10}$–$C_{16}$ alkyl polyglycoside, also commonly referred to as a D-glucopyranoside, (available from Henkel Ltd).

The nonionic surfactant can be present either singly, or a mixture of two or more nonionic surfactant compounds as defined above. Preferably, the total amount of non-ionic/cationic surfactants is from 1% to 10%.

Solvents usable in the compositions of present invention may be selected from solvents known in the art, of which volatile silicones, n-paraffins, alcohols, glycol ethers, propylene glycol, dipropylene glycol, iso-paraffins and amino methyl propanol are particularly suitable. Preferably, the solvent is present in an amount of from 0% to 8%.

An important function of the solvents included in the inventive formulations is the removal of fat and grease deposits. In principle, any solvent capable of removal of such deposits, which meets environmental and safety requirements and which may stably be included in the inventive formulations without deleteriously affecting desirable properties of the compositions, may be included.

It is desirable that at least a portion of the abrasive particles in the compositions of the invention should be maintained in suspension, in order to obviate the need for excessive shaking or agitation of the composition by the consumer prior to use. To this end, the compositions of the invention preferably include a thickening agent. The thickening agent may be such as to provide the composition with a generally Newtonian viscosity. Alternatively, the composition may be provided with a structured rheology, such as a shear thinning rheology. It is, of course, essential that the composition is pourable. Generally, for compositions with Newtonian viscosity, the viscosity will be in the range of from 200 to 600 Cps (as measured using a Brookfield DV-III viscometer). Where the composition has a structed rheology, the measured viscosity may be considerably higher. Suitable thickeners and rheology modifiers include polysaccharides such as hydroxy celluloses, carboxy methyl celluloses, such inorganic thickening agents based on clays as are compatible with quaternary ammonium antibacterial agents and other thickening media known in the art and compatible with quaternary ammonium antibacterial agents. Preferably, the thickener is present in an amount of from 0.1% to 8%.

The compositions of the invention may further include optional ingredients such as fragrances, colouring agents, silicas, preservatives, pH regulants, freeze-thaw stabilisers, opacifiers, optical brighteners and the like.

Test for Antibacterial Effect

A saturated solution of sodium bicarbonate was prepared containing 2.0% BTC 2125M which is believed to be a myristyl dimethyl benzyl ammonium chloride. The amount of BTC present is expressed as weight percent active material. To this solution further solid sodium bicarbonate was added and the mixture left overnight. The solid sodium bicarbonate was removed by filtration and the filtered solution was assessed for antimicrobial efficacy using prEN 1276 (proposed standard protocol for assessing disinfectants used in food, industrial, domestic and institutional areas), against *Pseudomonas aeruginosa* and *Staphylococcus aureus*. A control solution comprising 2.0% BTC 2125M only was similarly assessed. The results are shown in Table 1 below:

TABLE 1

| Sample | ME values on Consecutive Days Against: Pseudomona aeruginosa Staphylococcus aureus | | | |
|---|---|---|---|---|
| Test sample containing sodiuum bicarbonate and BTC 2125 (sample 1) | >5.0 | >5.0 | >5.0 | >5.0 |
| Control sample containing BTC 2125 only | >5.0 | >5.0 | >5.0 | >5.0 |

From these results, it can be seen that when solid sodium bicarbonate is added to a saturated solution of sodium bicarbonate containing a quaternary ammonium antibacterial agent, left to equilibrate overnight and the solid filtered off, within the limits of the test, no drop in antimicrobial activity of the residual solution is seen. A drop in antimicrobial activity would be expected if a significant amount of the quaternary ammonium compound became adsorbed on or otherwise deactivated by the particles of sodium bicarbonate.

The antibacterial effect of the quaternary ammonium antibacterial agents given in Table 2 below was tested in accordance with the method of Sample 1, but using 1.5% w/v (of active material) of the quaternary ammonium antibacterial agent in both the saturated sodium bicarbonate solution and in the control solution. In each case, the ME value against both *Ps. aeruginosa* and *S. aureus* was greater than 5.0.

TABLE 2

| Sample No | Quaternary ammonium antibacterial agent |
|---|---|
| 2 | Arquad 16–50 alkyl triethyl ammonium chloride |
| 3 | Pentonium 4 Br40-myristyl trimethyl ammonium bromide |
| 4 | Pentonium D050-dioctyl dimethyl ammonium chloride |
| 5 | Empigen Bac50-alkyl dimethyl benzyl ammonium chloride |

The following Examples illustrate the invention.

EXAMPLE 1

The following is illustrative of preferred formulations of the invention.

| Ingredients | Function | % w/w |
|---|---|---|
| Sodium bicarbonate | abrasive | 40 |
| Myristylalkonium chloride | antibacterial agent | 4% (2% active) |
| Polyethoxylated alcohol (90%) | surfactant | 4% |
| Dipropyleneglycol methyl ether | solvent | 4% |
| Hydroxyethyl cellulose | thickener | 0.5% |
| Water | | to 100% |

This formulation was found to be effective against a range of soils and was easily and effectively rinsed from the surface.

EXAMPLE 2

Abrasivity of Sodium Bicarbonate

Standard samples of polyacrylic poly(methyl methacrylate) were abraded under standard conditions with Extra Fine sodium bicarbonate, Course sodium bicarbonate, calcium carbonate (from Hopkin and Williams) and calcium carbonate (Durcal 40). The abrasion test was performed using a rotary abrasion apparatus with a 500 g weight spun at 5orpm for 15 minutes. Once the test was complete the samples were visually assessed. Results are shown in the Table below.

| Sample | Average Particle size | Abrasion Test Result |
|---|---|---|
| Extra Fine Sodium bicarbonate | 40 μm | 0 |
| Coarse sodium bicarbonate | 190 μm | 1 |
| Calcium carbonate (from Hopkin and Williams) | 30 μm | 2.5 |
| Calcium carbonate (Durcal 40) | 15 μm | 1 |

Abrasion Test Results were scored as follows:
No scratching-shiny surface 0
Some very fine scratches 1
Small scratches - some loss of surface shine 2
Some larger scratches 3
Badly scratched surface 4
Very badly scratched surface 5
loss of surface shine From these results it is apparent that sodium bicarbonate has advantageous non-scratching properties in comparison to the commonly used calcium carbonate abrasive.

I claim:

1. An aqueous antibacterial abrasive cleaning composition comprising, on a weight basis, from 8% to 80% of abrasive particles, selected from sodium catonate, sodium bicarbonate, sodium sesquicarbonate, sodium tripolyphosphate, sodium tetraborate decahydrate, potassium sulphate, sodium citrate, sodium chloride, potassium chloride, magnesium chloride, calcium chloride, sodium succinate, sodium adipate and sodium glutarate, from 0.5% to 25% in total of one or more surfactants selected from the group consisting of non-ionic surfactants, cationic surfactants and mixtures thereof, from 0.1% to 10% in total of at least one quaternary ammonium antibacterial agent of the formula:

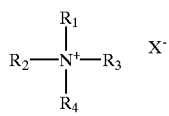

wherein
the cation portion of the molecule has a molecular weight of at least 165,
at least one of $R_1$, $R_2$, $R_3$ and $R_4$ is an optionally halogen-substituted hydrophobic aliphatic, arylaliphatic or aliphatic-aryl radical having from 6 to 26 carbon atoms,
the others of $R_1$, $R_2$, $R_3$ and $R_4$ are hydrocarbon radicals having a total of no more than 12 carbon atoms,
and X is a salt-forming anion,
from 0% to 15% of a solvent, and from 0.1 to 8% of a thickening agent,
wherein the abrasive particles are soluble in the composition and are present in an amount in excess of their saturation solubility.

2. A composition as claimed in claim 1, wherein undissolved abrasive particles represent at least 5% by weight of the composition.

3. A composition as claimed in claim 2 wherein the abrasive is selected from inorganic or organic water soluble salts of alkali or alkaline earth metals.

4. A composition as claimed in claim 3 wherein the salt comprising the abrasive particles is present in total amount of 15% to 60% by weight of the composition.

5. A composition as claimed in claim 1 wherein the abrasive particles are sodium bicarbonate.

6. A composition as claimed in claim 1 wherein the quaternary ammonium antibacterial agent is present in an amount of 0.1% to 4%.

7. A composition as claimed in claim 1 wherein the quaternary ammonium antibacterial agent comprises decyl trimethyl ammonium chloride, decyl dimethyl benzyl ammonium chloride, lauryl trimethyl ammonium chloride, lauryl dimethyl benzyl ammonium chloride, myristyl trimethyl ammonium chloride, myristyl dimethyl benzyl ammonium chloride, myristyl trimethyl ammonium bromide, cetyl trimethyl ammonium chloride, cetyl trimethyl ammonium bromide, dioctyl dimethyl ammonium chloride, didecyl dimethyl ammonium chloride or dilauryl dimethyl ammonium chloride.

8. A composition as claimed in claim 1 in which the quaternary ammonium antibacterial agent comprises one or more compounds of the formula:

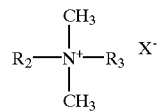

wherein
each of $R_2$ and $R_3$ is $C_8$–$C_{12}$ alkyl,
or $R_2$ is $C_{12}$–$C_{16}$ alkyl, $C_8$–$C_{18}$ alkylethoxy or $C_8$-$C_{18}$ alkylphenolethoxy and $R_3$ is benzyl, and
X is chloride, bromide, iodide or methosulphate.

9. A composition as claimed in claim 1 wherein the surfactants are non-ionic surfactants and are present in total amount from 1% to 10%.

10. A composition as claimed in claim 9 wherein the non-ionic surfactant is selected from alcohol ethoxylates, alkyl phenol ethoxylates, amine ethoxylates, fatty acid ethoxylates, block copolymers, ester ethoxylates, glyceride ethoxylates, alkoxylates, alkyloamides and amine oxides.

11. A composition as claimed in claim 1 wherein the solvent is selected from volatile silicones, n-paraffins, alcohols, glycol ethers, propylene glycol, dipropylene glycol, iso-paraffins and amino-methyl propanol.

12. A composition as claimed in claim 11 wherein the solvent is present in an amount of from 0% to 8%.

13. A composition as claimed in claim 1 wherein the composition has a viscosity of from 200 to 600 cps.

14. A composition as claimed in claim 1 wherein the composition has a structured rheology.

15. A composition as claimed in claim 1 wherein the thickener is selected from polysaccharides and inorganic clay-based agents which are compatible with quaternary ammonium antibacterial agents.

* * * * *

UNITED STATES PATENT AND TRADEMARK OFFICE
CERTIFICATE OF CORRECTION

PATENT NO. : 6,458,753 B1
DATED : October 1, 2002
INVENTOR(S) : Nicholas Haylett It is certified that error appears in the above-identified patent and that said Letters Patent is hereby corrected as shown below:

<u>Column 10,</u>
Line 37, please replace the word "catonate" with -- carbonate --

Signed and Sealed this

Eighteenth Day of February, 2003

JAMES E. ROGAN
*Director of the United States Patent and Trademark Office*